United States Patent [19]

Fujimura et al.

[11] 4,409,234
[45] Oct. 11, 1983

[54] PYRAZOLOINDAZOLE DERIVATIVES AND BRONCHODILATING COMPOSITION

[75] Inventors: Yasuo Fujimura, Saitama; Sadao Tanaka, Tokyo; Isao Matsunaga, Tokyo; Yasuyuki Shiraki, Tokyo; Yugo Ikeda, Sayama; Tamotsu Yamazaki, Tokorozawa; Yasuhiro Ohba, Kawasaki; Shun-ichi Hata, Yokohama; Minoru Shindo, Tokyo; Kazushige Sakai, Tokyo, all of Japan

[73] Assignee: Chugai Seiyaku Kabushiki Kaisha, Tokyo, Japan

[21] Appl. No.: 384,861

[22] Filed: Jun. 3, 1982

Related U.S. Application Data

[63] Continuation of Ser. No. 165,943, Jul. 3, 1980, abandoned.

[30] Foreign Application Priority Data

Jul. 16, 1979 [JP] Japan .................................. 54-89311

[51] Int. Cl.³ .................. C07D 487/04; A61K 31/415
[52] U.S. Cl. .............................. 424/273 N; 548/371; 548/372
[58] Field of Search ............................. 548/371, 372; 424/273 N

[56] References Cited

U.S. PATENT DOCUMENTS 3,825,556  7/1974  Minieri .............................. 548/372

FOREIGN PATENT DOCUMENTS 23633  3/1981  European Pat. Off. .

OTHER PUBLICATIONS

Elguero et al., Bull. Soc. Chim. Fr. 1969, No. 6, pp. 2064–2076.
Solomons et al., J. Heterocycl. Chem. 1971, vol. 8(3), pp. 489–491.
Palazzo et al., Chem. Abst. 1970, vol. 72, No. 90.366n.

Primary Examiner—Henry R. Jiles
Assistant Examiner—Natalia Harkaway
Attorney, Agent, or Firm—Browdy and Neimark

[57] ABSTRACT

Novel pyrazoloindazole derivatives of the formula

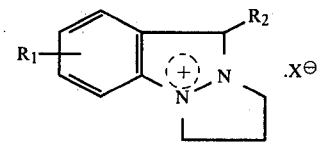

wherein $R_1$ is a hydrogen atom, halogen atom, a hydroxyl group, a lower alkyl group, a lower alkoxyl group or benzyloxyl group; $R_2$ is a hydrogen atom, a halogen atom, a lower alkyl group or phenyl group (provided $R_1$ and $R_2$ are not hydrogen at the same time); and $X^\ominus$ is a halide ion, a hydroxide ion, a methanesulfonate ion, a p-toluene sulfonate ion, a sulfate ion, a nitrate ion, a carbonate ion, an acetate ion, a benzoate ion or a salicylate ion, a process for preparing the derivatives, and a pharmaceutical composition containing the same are disclosed. The derivatives have good bronchodilating action for human without exhibiting substantially bad effects on the functioning of heart, and therefore, they are useful as a drug.

23 Claims, No Drawings

PYRAZOLOINDAZOLE DERIVATIVES AND BRONCHODILATING COMPOSITION

This is a continuation, of application Ser. No. 165,943 filed July 3, 1980, now abandoned.

This invention relates to compounds represented by the formula

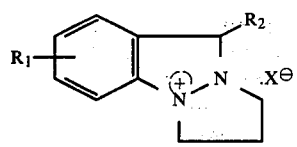

wherein $R_1$ is a hydrogen atom, halogen atom, a hydroxyl group, a lower alkyl group, a lower alkoxyl group or benzyloxyl group; $R_2$ is a hydrogen atom, a halogen atom, a lower alkyl group or phenyl group (provided $R_1$ and $R_2$ are not hydrogen at the same time); and $X^\ominus$ is a halide ion, a hydroxide ion, a methanesulfonate ion, a p-toluenesulfonate ion, a sulfate ion, a nitrate ion, a carbonate ion, an acetate ion, and benzoate ion or a salicylate ion. It also relates to a process for preparing the compounds defined above, and a pharmaceutical composition containing the same.

It has now been found that the pyrazoloindazole derivatives represented by the formula (I) above have good bronchodilating action for humans without exhibiting substantially bad effects on the functioning of heart. Therefore, the derivatives are believed to be useful as a drug.

According to this invention, the pyrazoloindazole derivatives of this invention are prepared by cyclizing a compound of the formula

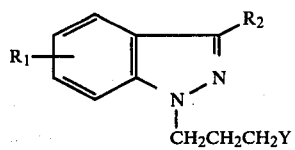

wherein $R_1$ and $R_2$ are as defined above and Y is a halogen atom, or a compound of the formula

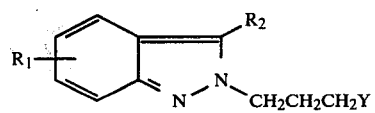

wherein $R_1$, $R_2$ and Y are as defined above, and optionally, exchanging a counter ion represented with $X^\ominus$ in the formula (I) with another counter ion.

Although the cyclization reaction progresses by merely allowing a mixture of the compound (II) with the compound (III) to stand at room temperature when one of the compounds is oily, it is preferable to heat the reaction mixture in order to shorten the reaction time and increase the yield. The heating is usually effected at 50° to 150° C. The reaction is preferably carried out in the presence of a solvent, such as acetone, benzene, toluene, xylene or the like, because the use of a solvent makes the reaction easy to control and separation of the product after completion of the reaction can be done by a simple process, for example, by filtration.

Either of the starting compounds (II) and (III) used in this invention process can be prepared by condensing a compound of the formula

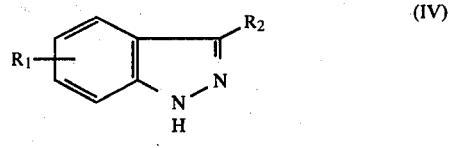

wherein $R_1$ and $R_2$ are as defined above, with 1,3-dihalogenopropane in an inert solvent such as dimethylformamide in the presence of a promoter such as sodium hydride. Alternatively, the reaction of the compound (IV) with 1,3-dihalogenopropane may be carried out with use of a phase transfer catalyst in a mixed solvent of aqueous sodium hydroxide with an organic solvent such as benzene, toluene, xylene, etc.

By any of the reactions the compounds (II) and (III) are obtained as a mixture. Each of the compounds can be isolated by a column chromatography, but usually they are used without separating.

Among the thus prepared compounds, those of the formula (I) wherein $R_1$ is a benzyloxyl group may be subjected to catalytic reduction with a catalyst such as palladium-charcoal in an organic solvent such as methanol, ethanol, tetrahydrofuran, etc. at a temperature between room temperature and 50° C. thereby forming the corresponding hydroxides. If necessary, the counter ion of the compound prepared can be exchanged with other species of ion through, for example, ion exchange resin treatment.

The compounds prepared by the method above have good bronchodilating action without detectable bad effects on heart functioning. Therefore, they are useful as a drug.

Each compound of this invention is formulated in any convention manner into a pharmaceutical composition.

This invention is more specifically illustrated by the following Examples and Experiments, but should not be construed as being limited thereby.

EXAMPLE 1

(a) To a solution of 5-benzyloxyindazole (30 g) in dimethylformamide (150 ml), 50% sodium hydride (6.7 g) was added and the mixture was stirred at room temperature for 10 minutes. The solution was then added dropwise to 150 ml of dimethylformamide containing 1-bromo-3-chloropropane (30 g) while cooling with ice, and, after stirring at room temperature for 30 minutes, the mixture was extracted with benzene. The extract was washed with water, dried over anhydrous sodium sulfate, and distilled to remove the solvent used. The residue was chromatographed with a column filled with silica gel to give 16 g of 1-(3'-chloropropyl)-5-benzyloxyindazole (m. p. 65°–66° C.) and 4.5 g of 2-(3'-chloropropyl)-5-benzyloxyindazole (m.p. 97°–98° C.).

(b) 1-(3'-Chloropropyl)-5-benzyloxyindazole (15 g) obtained in (a) above was heated to melt. It solidified upon cooling, and the solidified product was separated, suspended in acetone, and recovered by filtration to give 14.5 g of 2,3-dihydro-7-benzyloxy-1H-pyrazolo[1,2-a]indazolium chloride. After recrystallization from isobutanol, the product had a melting point of 166° to 168° C.

Analysis:

Calcd. for C₁₇H₁₇N₂OCl: C, 67.88; H, 5.70; N, 9.31 (%) Found: C, 67.73; H, 5.85; N, 9.17 (%).

EXAMPLE 2

2-(3'-Chloropropyl)-5-benzyloxyindazole (3.5 g) obtained as in Example 1 (a) was treated as in Example 1 (b) to give 3 g of 2,3-dihydro-7-benzyloxy-1H-pyrazolo[1,2-a]indazolium chloride. The product did not exhibit any drop in the melting point, even after it was mixed with the product of Example 1. Also, IR and NMR of the product were the same as those of the product of Example 1.

EXAMPLE 3

2,3-Dihydro-7-benzyloxy-1H-pyrazolo[1,2-a]indazolium chloride (6 g) obtained in Examples 1 and 2 was dissolved in methanol (100 ml) and catalytically reduced by adding 10% palladium-charcoal (0.6 g) to the solution, to give 3.5 g of 2,3-dihydro-7-hydroxy-1H-pyrazolo[1,2-a]indazolium chloride. After recrystallization from isobutanol, the product had a melting point of 278° to 279° C. (decomposition).

Analysis:

Calcd. for C₁₀H₁₁N₂OCl: C, 57.01; H, 5.26; N, 13.30 (%) Found: C, 57.16; H, 5.21; N, 13.18 (%)

EXAMPLE 4

To a solution of 5-methyl-3-phenylindazole (10.4 g) in dimethylformamide (60 ml), 50% sodium hydride (2.5 g) was added and the mixture was stirred at room temperature for 10 minutes. The reaction mixture was then added dropwise to dimethylformamide (20 ml) containing 1,3-dibromopropane (25 g) while cooling with ice, and the resulting mixture was stirred at room temperature for 30 minutes. The mixture was extracted with xylene (120 ml), and the extract was washed with water, dried over anhydrous sodium sulfate and heated at reflux for 2 hours. The resulting precipitate was recovered by filtration, and washed with acetone to give 9.2 g of 2,3-dihydro-7-methyl-9-phenyl-1H-pyrazolo[1,2-a]indazolium bromide. After recrystallization from isobutanol, the product had a melting point of 237° to 241° C. (decomposition).

Analysis:

Calcd. for C₁₇H₁₇N₂br: C, 62.02; H, 5.20; N, 8.51 (%) Found: C, 61.80; H, 5,27; N, 8.36 (%)

EXAMPLE 5

5-Methyl-3-phenylindazole (400 g) was dissolved in toluene (1 l) and 1,3-dibromopropane (600 ml), and to the solution were added triethylbenzylammonium chloride (40 g) and 30% aqueous sodium hydroxide (800 ml). The mixture was heated at 60° C. for 30 minutes while stirring and the resulting organic layer was separated. The layer was washed with water, dried over sodium sulfate and then heated at reflux for 3 hours. The precipitate was recovered by filtration and washed with toluene to give 319 g of 2,3-dihydro-7-methyl-9-phenyl-1H-pyrazolo[1,2-a]indazolium bromide. The product which was recrystallized from water had a decomposition point of 239° C.

Analysis:

Calcd. for C₁₇H₁₇N₂Br.1/2H₂O: C, 60.37; H, 5.36; N, 8.28 (%) Found: C, 60.62; H, 5.07; N, 8.22 (%)

EXAMPLE 6

An aqueous solution (10 ml) of 2,3-dihydro-7methyl-9-phenyl-1H-pyrazolo[1,2-a]indazolium bromide (1 g) obtained in Example 4 was fed into a column filled with 30 g of ion exchange resin, Amberlite IRA-401 (Cl⁻type) (manufactured by Rohm & Haas Co.) and eluted with distilled water (1 l). The eluate was concentrated to give 0.8 g of 2,3-dihydro-7-methyl-9-phenyl-1H-pyrazolo[1,2-a]indazolium chloride. After recrystallization from isobutanol, the product had a melting point of 178° to 180° C.

Analysis:

Calcd. for C₁₇H₁₇N₂Cl.1/2H₂O: C, 69.50; H, 6.18; N, 9.45 (%) Found: C, 69.71; H, 5.86; N, 9.49 (%).

By a procedure similar to that above using the ion-exchange resin with a different type of counter ion, 2,3-dihydro-7-methyl-9-phenyl-1H-pyrazolo[1,2-a]indazolium methanesulfonate, sulfate, nitrate, carbonate, acetate, para-toluene-sulfonate, benzoate, salycilate or hydroxide was obtained.

EXAMPLES 7–23

By a procedure similar to that of Example 4, the following products were obtained.

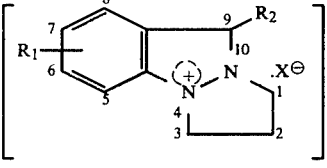

| Examples | R₁ | R₂ | X | m.p. (°C.) |
|---|---|---|---|---|
| 7 | 7-Cl |  | Cl | 235–236 (decomposition) |
| 8 | H | " | " | 218–220 (decomposition) |
| 9 | 7-Br | " | " | 226–228 (decomposition) |
| 10 | 7-Br | Br | Cl | 224–226 (decomposition) |
| 11 | H | CH₃ | Br | 216–218 |
| 12 | 6-CH₃ | H | Cl | 228–229 |
| 13 | 7-OCH₃ | " | " | 180–182 |
| 14 | 7-CH₃ | " | " | 212–214 |
| 15 | 8-CH₃ | " | " | 257–258 |
| 16 | 7-CH₃ | CH₃ | Br | 252–254 (decomposition) |
| 17 | " | C₂H₅ | " | 180–182 |
| 18 | " | n-C₃H₇ | " | 152–155 |
| 19 | " |  | CH₃SO₃ | 189–190° C. |
| 20 | " | " | CH₃COO | 82–84° C. |
| 21 | " | " | 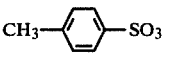 | 116–121° C. |
| 22 | " | " | 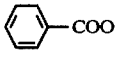 | 120–122° C. |
| 23 | " | " | 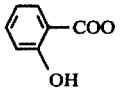 | 143–144° C. |

EXPERIMENT

By the method of Himori et al (Br. J. Pharmac. (1976), 56, 293–299), a tracheal tube equipped with a water-filled cuff was inserted into the trachea of a dog and the change of pressure put on the cuff was measured by a pressure transducer which was connected with the cuff, to determine the effect of the test compound on dilatation of tracheal muscles.

Each of the test compounds and the controls listed in the Table below was dissolved in physiological saline, and injected into the tracheal branch of the cranial thyroid artery in 100 mg/kg. 0.11 ml over 10 sec.

The results are shown in the Table below.

TABLE

| Test compound | Intralumineal Pressure % change | Prolonged time | Ratio[1] |
|---|---|---|---|
| Compound of Example 4 | 100% | >60 min | >20 |
| Compound of Example 6 | 100% | >60 min | >20 |
| Compound of Example 7 | 98% | 15 min | 4.77 |
| Compound of Example 8 | 55.5% | 6 min 20 sec | 1.14 |
| Compound of Example 16 | 60% | 3 min | 0.58 |
| Compound of Example 17 | 100% | 6 min 30 sec | 2.11 |
| Compound of Example 18 | 94% | 7 min 30 sec | 2.29 |
| Compound of Example 19 | 100% | >60 min | >20 |
| Compound of Example 20 | 100% | >60 min | >20 |
| Noradrenaline[2] | 92.5% | 3 min 20 sec | 1.00 |
| Isoproternal[3] | 100% | 6 min | 1.95 |

Remarks:
[1]The ratio was calculated on the assumption that maximum % change × prolonged time on noradrenaline is 1.00.
[2]Administered in a dose of 1 μg/kg
[3]Administered in a dose of 0.3 μg/kg

What is claimed is:
1. A compound represented by the formula

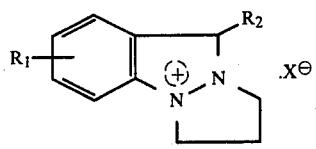

wherein $R_1$ is a hydrogen atom, halogen atom, a hydroxyl group, a lower alkyl group, a lower alkoxyl group or benzyloxy group; $R_2$ is a hydrogen atom, a halogen atom, a lower alkyl group or phenyl group (provided $R_1$ and $R_2$ are not hydrogen at the same time); and $X^\ominus$ is a halide ion, a hydroxide ion, a methanesulfonate ion, a p-toluenesulfonate ion, a sulfate ion, a nitrate ion, a carbonate ion, an acetate ion, a benzoate ion or a salicylate ion.

2. 7-Benzyloxy-2,3-dihydro-1H-pyrazolo[1,2-a]indazolium chloride according to claim 1.
3. 2,3-Dihydro-7-hydroxy-1H-pyrazolo[1,2-a]indazolium chloride according to claim 1.
4. 2,3-Dihydro-7-methyl-9-phenyl-1H-pyrazolo[1,2-a]indazolium bromide according to claim 1.
5. 2,3-Dihydro-7-methyl-9-phenyl-1H-pyrazolo[1,2-a]indazolium chloride according to claim 1.
6. 7-Chloro-2,3-dihydro-9-phenyl-1H-pyrazolo[1,2-a]indazolium chloride according to claim 1.
7. 2,3-Dihydro-9-phenyl-1H-pyrazolo[1,2-a]indazolium chloride according to claim 1.
8. 7-Bromo-2,3-dihydro-9-phenyl-1H-pyrazolo[1,2-a]indazolium chloride according to claim 1.
9. 7,9-Dibromo-2,3-dihydro-1H-pyrazolo[1,2-a]indazolium chloride according to claim 1.
10. 2,3-Dihydro-9-methyl-1H-pyrazolo[1,2-a]indazolium bromide according to claim 1.
11. 2,3-Dihydro-6-methyl-1H-pyrazolo[1,2-a]indazolium chloride according to claim 1.
12. 2,3-Dihydro-7-methoxy-1H-pyrazolo[1,2-a]indazolium chloride according to claim 1.
13. 2,3-Dihydro-7-methyl-1H-pyrazolo[1,2-a]indazolium chloride according to claim 1.
14. 2,3-Dihydro-8-methyl-1H-pyrazolo[1,2-a]indazolium chloride according to claim 1.
15. 2,3-Dihydro-7,9-dimethyl-1H-pyrazolo[1,2-a]indazolium bromide according to claim 1.
16. 2,3-Dihydro-9-ethyl-7-methyl-1H-pyrazolo[1,2-a]indazolium bromide according to claim 1.
17. 9-Butyl-2,3-dihydro-7-methyl-1H-pyrazolo[1,2-a]indazolium bromide according to claim 1.
18. 2,3-Dihydro-7-methyl-9-phenyl-1H-pyrazolo[1,2-a]indazolium methanesulfonate according to claim 1.
19. 2,3-Dihydro-7-methyl-9-phenyl-1H-pyrazolo[1,2-a]indazolium acetate according to claim 1.
20. 2,3-Dihydro-7-methyl-9-phenyl-1H-pyrazolo[1,2-a]indazolium paratoluenesulfonate according to claim 1.
21. 2,3-Dihydro-7-methyl-9-phenyl-1H-pyrazolo[1,2-a]indazolium benzoate according to claim 1.
22. 2,3-Dihydro-7-methyl-9-phenyl-1H-pyrazolo[1,2-a]indazolium salicylate according to claim 1.
23. A bronchodilating composition comprising an amount effective for bronchodilation of a compound according to claim 1 and a pharmaceutically acceptable carrier.

* * * * *